United States Patent [19]

Sjoerdsma

[11] 4,336,054

[45] Jun. 22, 1982

[54] METHOD OF INHIBITING ALGAE

[75] Inventor: Albert Sjoerdsma, Cincinnati, Ohio

[73] Assignee: Merrell Dow Pharmaceuticals Inc., Cincinnati, Ohio

[21] Appl. No.: 246,569

[22] Filed: Mar. 23, 1981

Related U.S. Application Data

[63] Continuation-in-part of Ser. No. 95,347, Nov. 19, 1979, abandoned.

[51] Int. Cl.$^3$ .................... A01N 37/02; A01N 37/06
[52] U.S. Cl. ........................................................ 71/67
[58] Field of Search ........................................... 71/67

[56] References Cited

U.S. PATENT DOCUMENTS 2,890,246  6/1959  McKinney et al. .................. 71/67
3,466,162  9/1969  Gloor et al. ......................... 71/67

OTHER PUBLICATIONS

Brachet et al., C. R. Acad. Sci., Paris, Serie D 287, (1978), pp. 1289–1292.

*Primary Examiner*—Catherine L. Mills
*Attorney, Agent, or Firm*—William J. Stein; Raymond A. McDonald; John J. Kolano

[57] ABSTRACT

α-Substituted amines and α-substituted-α-amino acids are described which are useful in controlling the growth of algae.

5 Claims, No Drawings

METHOD OF INHIBITING ALGAE

DESCRIPTION

This application is a continuation-in-part of U.S. Ser. No. 95,347, filed Nov. 19, 1979, abandoned.

TECHNICAL FIELD

This invention relates to certain α-substituted amines and α-substituted-α-amino acids which are useful in controlling or inhibiting the growth of algae.

BACKGROUND ART

Polyamines have been implicated in many aspects of cell division. Impairment of the biosynthesis of polyamines by means of enzyme inhibitors is believed to cause a decrease in cell proliferation in mammals. Although the physiological role of polyamines has not been clearly delineated, there is evidence to suggest their involvement with cell division and growth, H. G. Williams-Ashman et al., The Italian J. Biochem. 25, 5–32 (1976), A. Raina and J. Janne, Med. Biol. 53, 121–147 (1975) and D. H. Russell, Life Sciences 13, 1635–1647 (1973).

Polyamines are also known to be essential growth factors for certain microorganisms, as for example *E. coli*, Enterobacter, Klebsiella, *Staphylococcus aureus, C. cadaveris, Salmonella typhosa* and *Haemophilus parainfluenza*. There between polyamine formation and the activity of the decarboxylase enzymes of ornithine, S-adenosylmethionine, arginine and lysine. The term polyamine is taken to include the diamine putrescine and the polyamines spermidine and spermine. Putrescine is the decarboxylation product of ornithine, catalyzed by ornithine decarboxylase. Putrescine formation may also occur by decarboxylation of arginine to form agmatine which is hydrolyzed to give putrescine and urea. Arginine is also involved in ornithine formation by action of the enzyme arginase. Activation of methionine by S-adenosylmethionine synthetase forms S-adenosylmethionine which is decarboxylated, after which the propylamine moiety of activated methionine may be transferred to putrescine to form spermidine or the propylamine moiety may be transferred to spermidine to form spermine. Hence, putrescine serves as a precursor to spermidine and spermine and additionally has been shown to have a marked regulatory effect upon the polyamine biosynthetic pathway in that it has been shown that increased synthesis of putrescine is the first indication that a tissue will undergo renewed growth processes. Cadaverine which is the decarboxylation product of lysine has been shown to stimulate the activity of S-adenosylmethionine decarboxylase and is known to be essential to growth processes of many microorganisms, for example, *H. parainfluenza*.

Very little is known of the role of polyamines in algal growth. The occurrence of polyamines in algae has been reported, but little is known about their biosynthetic pathways in algae. Brachet et al., C.R. Acad. Sc. Paris, Serie D, 287, 1289–92 (1978), has shown that DL-α-methylornithine arrests development of sea Urchine eggs, and prevents the regeneration of the algae, *Acetabularia mediterranea*, via the inhibition of nuclear RNA synthesis.

SUMMARY OF THE INVENTION

I have discovered that compounds belonging to a class of irreversible inhibitors of ornithine decarboxylase and S-adenosylmethionine decarboxylase are useful in inhibiting the growth of algae. Moreover, this inhibition occurs among the blue-green, green, the diatom and the pigmented flagellate groups of algae. More particularly, the compounds useful in the practice of this invention are α-substituted amines or α-substituted-α-amino acids having the general formula

 (I)

wherein $R_1$ is hydrogen or carboxy; Y is selected from the group consisting of $CH_2F$, $CHF_2$, $CF_3$ and $C{\equiv}CH$; Z is selected from the group consisting of $H_2N\text{-}(CH_2)_3$,

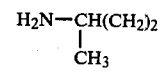

and $H_2N\text{-}CH_2CH{=}CH$; with the proviso that when $R_1$ is hydrogen, Y cannot be $CF_3$ and Z must be

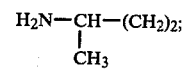

and the salts and individual optical isomers thereof.

Actively growing algae when placed in contact with these compounds demonstrate a reduction in their rate of proliferation and growth, enabling these compounds to be useful for the control of algae in industrial and recreational water supplies.

DETAILED DESCRIPTION OF THE INVENTION

In general formula (I) above the symbol $R_1$ is represented either by hydrogen or a carboxyl group. Where the symbol $R_1$ is hydrogen a class of α-substituted amines is delineated. Where the symbol $R_1$ is the carboxyl group, a class of α-substituted-α-amino acids is delineated.

The symbol Y represents either an acetylenic group or a fluoro-substituted methyl group. The fluoro-substituted methyl groups are illustrated by the monofluoromethyl, difluoromethyl or trifluoromethyl radicals.

The symbol Z represents either the 3-aminopropyl group, the 3-amino-3-methylpropyl group or the 3-amino-1-propylene group. The saturated groups, viz. the 3-aminopropyl group and the 3-amino-3-methylpropyl group represent the preferred side chains.

The proviso limitation is intended to exclude certain classes of diamines from the scope of compounds encompassing this invention. Thus excluded from the invention via the proviso limitation are α-substituted diamines wherein the symbol Z is the 3-aminopropyl group or the 3-amino-1-propylene group having the general formula

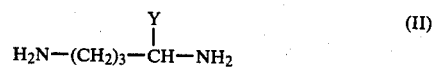 (II)

and

-continued

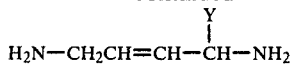

wherein the symbol Y is as previously defined.

Specifically excluded from the remaining α-substituted diamines is the species wherein the symbol Y represents the trifluoromethyl group. Thus, compound (IV) 4-methyl-1-trifluoromethyl-1,4-butanediamine, is specifically excluded from the scope of compounds which can be usefully employed.

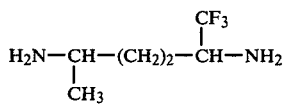

Included within the scope of compounds that can be employed are α-substituted amino acids having the formula:

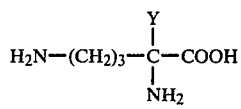

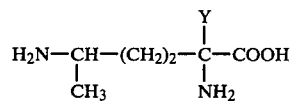

and

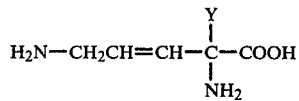

In compounds (V), (VI) and (VII) the symbol Y is as previously defined.

The α-substituted amines which are included within the scope of compounds that can be usefully employed in the practice of this invention can be defined by the general formula

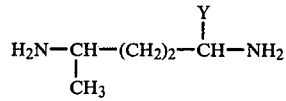

wherein the symbol Y represents the CH$_2$F, CHF$_2$ and C≡CH groups, but in the case of the diamines excludes the CF$_3$ group.

Illustrative examples of the salts of the compounds of this invention include non-toxic acid addition salts formed with inorganic acids, such as, hydrochloric, hydrobromic, sulfuric and phosphoric acid, and organic acids, such as, methane sulfonic, salicyclic, maleic, malonic, tartaric, citric, cyclamic and ascorbic acids.

A preferred class of compounds of this invention are those compounds in which the symbol Y represents the difluoromethyl group. Another preferred class of compounds is delineated where the symbol Z represents the 3-aminopropyl moiety or the 3-amino-3-methylpropyl moiety.

In addition to the salts indicated above, the term salts is taken to include those internal salts or zwitter-ions of those compounds of formula I above that are amphoteric in nature. Moreover, whereas the optical configuration for the compounds described herein is not specifically designated, it is recognized that the α-carbon atom possesses an asymmetric center and that individual optical isomers of these compounds exist. Accordingly, both the d- and l-optical isomers as well as the racemic mixtures are contemplated as being within the scope of this invention.

Lactam formation can occur where the symbol R$_1$ represents the carboxyl group and the symbol Z represents the 3-aminopropyl moiety or the 3-amino-3-methylpropyl moiety as represented by the following general formula

In the above general formula the symbol Y is as originally described above. Where the symbol Z represents the 3-amino-3-methylpropyl moiety, the (CH$_2$)$_3$ group in formula (IX) above can be additionally substituted with a 3-methyl group.

Illustrative examples of compounds useful in accordance with the teachings of this invention include:

2,5-diamino-2-(fluoromethyl)pentanoic acid
2,5-diamino-2-(difluoromethyl)pentanoic acid
2,5-diamino-2-(trifluoromethyl)pentanoic acid
2,5-diamino-2-(ethynyl)pentanoic acid
2,5-diamino-2-fluoromethyl-5-methylpentanoic acid
2,5-diamino-2-difluoromethyl-5-methylpentanoic acid
2,5-diamino-2-trifluoromethyl-5-methylpentanoic acid
2,5-diamino-2-ethynyl-5-methylpentanoic acid
2,5-diamino-2-fluoromethyl-3-pentenoic acid
2,5-diamino-2-difluoromethyl-3-pentenoic acid
2,5-diamino-2-trifluoromethyl-3-pentenoic acid
2,5-diamino-2-ethynyl-3-pentenoic acid
1-fluoromethyl-4-methyl-1,4-butanediamine
1-difluoromethyl-4-methyl-1,4-butanediamine
1-ethynyl-4-methyl-1,4-butanediamine The compounds of general formula I wherein Z is

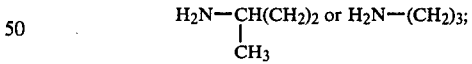

Y is CH$_2$F, CHF$_2$ and CF$_3$, and R$_1$ is carboxy are prepared by treating respectively an ester derivative of ornithine or lysine, wherein the amino groups are suitably protected, with a strong base to form the carbanion intermediate which is reacted with a suitable halomethyl-halo alkylating reagent in an aprotic solvent, such as, dimethylsulfoxide, dimethylformamide, dimethylacetamide, benzene, toluene, ethers, such as, tetrahydrofuran, diethyl ether or dioxane and in the presence of hexamethylphosphortriamide when Y is other than F$_2$CH- at a temperature of about −120° C. to 120° C., preferably about 25° to 50° C. for about ½ hour to 48 hours followed by acid or base hydrolysis as represented by the following reaction sequence.

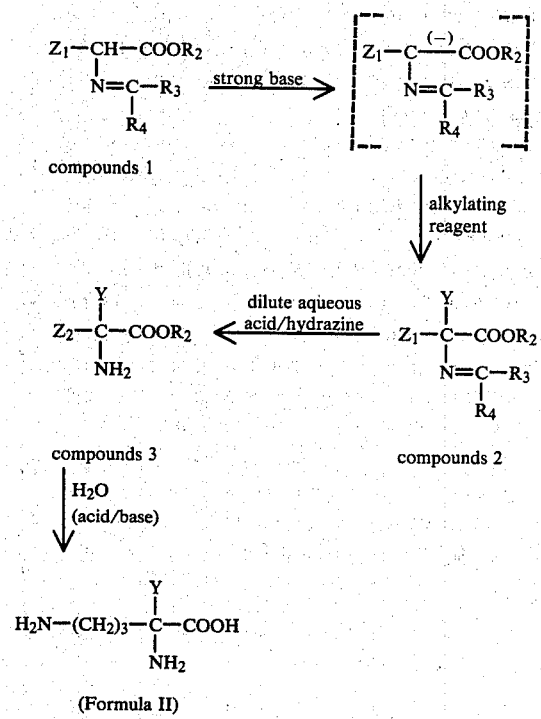

compounds 1 alkylating reagent compounds 2 dilute aqueous acid/hydrazine compounds 3

H₂O (acid/base)

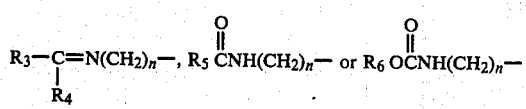

(Formula II)

In the above reaction sequence Y is $FCH_2-$, $F_2CH-$, $F_3C-$; $R_2$ is a lower alkyl group, for example, methyl, ethyl, isopropyl, n-propyl or n-butyl; $R_3$ is hydrogen, phenyl, a straight or branched alkyl group having from 1 to 8 carbon atoms, methoxy or ethoxy; $R_4$ is phenyl or a straight or branched alkyl group of from 1 to 8 carbon atoms; or $R_3$ and $R_4$ taken together may form an alkylene group of from 5 to 7 carbon atoms, that is, $-CH_2-(CH_2)_m-CH_2-$ wherein m is an integer of from 3 to 5. Illustrative examples of straight or branched alkyl groups of from 1 to 8 carbon atoms which $R_3$ and $R_4$ may represent are, for example, methyl, ethyl, n-propyl, isopropyl, n-butyl, tert-butyl, n-pentyl, neopentyl or triethylmethyl; $Z_1$ is

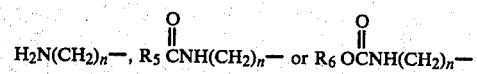

wherein n is the integer 3 or 4; $R_3$ and $R_4$ are the same and have the meanings defined above; and each of $R_5$ and $R_6$ is phenyl, benzyl or a lower alkyl group of from 1 to 4 carbon atoms that is straight or branched, for example, methyl, ethyl or isopropyl; $Z_2$ is $$H_2N(CH_2)_n-, \quad R_5\overset{O}{\overset{\|}{C}}NH(CH_2)_n- \quad \text{or} \quad R_6\overset{O}{\overset{\|}{O}}CNH(CH_2)_n-$$

wherein n, $R_5$ and $R_6$ have the above defined meanings.

Suitable strong bases which may be employed in the above reaction sequence to form the carbanion intermediate are those which will abstract a proton from the carbon atom alpha to the carboxy group, such as, alkyl lithium, for example, butyl lithium or phenyl lithium, lithium di-alkylamide, for example, lithium diisopropylamide, lithium amide, tertiary potassium butylate, sodium amide, metal hydrides, for example, sodium hydride or potassium hydride, tertiary amines, such as, triethylamine, lithium acetylide or dilithium acetylide. Lithium acetylide, dilithium acetylide, sodium hydride, and lithium diisopropylamide are particularly preferred bases.

Suitable alkylating reagents which may be employed in the above reaction sequence are illustratively chlorofluoromethane, bromofluoromethane, fluoroiodomethane, chlorodifluoromethane, bromodifluoromethane, difluoroiodomethane, bromotrifluoromethane, chlorotrifluoromethane, trifluoroiodomethane, bromochloromethane, dichloromethane, chloroiodomethane, bromodichloromethane and dichloroiodomethane. The alkylating reagents are known in the art.

Removal of the protecting groups of the amine and carboxylic function may be achieved in one step by treatment of compounds 2 with aqueous acid, for example, hydrochloric acid or toluenesulfonic acid at a temperature of about 0° to 100° C. for about 4 to 24 hours to give compounds of general Formula II. It is preferred to remove first the protecting groups of the amine function(s) of compounds 2 when said functions are protected as a Schiff's base by treating compounds 2 with dilute aqueous acid, for example, hydrochloric acid or with hydrazine or phenylhydrazine in solvents, such as, lower alcohols, for example, methanol or ethanol, ethers, chlorinated hydrocarbons, benzene and water. Removal of the protecting groups of the carboxylic functions and the amine groups when the amine groups are protected other than as a Schiff's base is achieved by treatment of compounds 3 with concentrated aqueous acids, for example, hydrobromic acid at a temperature of about 0° to 100° C. or in aqueous bases, for example, ammonium hydroxide.

The amine protected ester derivatives, that is, compounds 1, wherein $R_3$ is other then methoxy or ethoxy, are prepared by treating an appropriate amino acid water with a carbonyl bearing compound to form a Schiff's base in a generally known manner, specifically: (a) when $R_3$ is hydrogen, by treating the appropriate amino acid water with benzaldehyde or an alkanal having from 1 to 9 carbon atoms being straight or branched, for example, 1-propanal, 1-butanal, 2,2-dimethylpropan-1-al or 2,2-diethylbutan-1-al; (b) when $R_3$ is phenyl by treating the appropriate amino acid ester with benzophenone or phenyl alkyl ketone wherein the alkyl moiety has from 1 to 8 carbon atoms and is straight or branched, for example, phenyl methyl ketone, phenyl ethyl ketone, phenyl isopropyl ketone, phenyl n-butyl ketone or phenyl tert-butyl ketone; and (c) when $R_3$ is a straight or branched alkyl group having from 1 to 8 carbon atoms, treating the appropriate amino acid ester with a phenyl alkyl ketone as described above or with a di-alkyl ketone wherein each alkyl moiety has from 1 to 8 carbon atoms and is straight or branched, for example, dimethyl ketone, diethyl ketone, methyl isopropyl ketone, di-n-butyl ketone or methyl tert-butyl ketone. The carbonyl bearing compounds are known in the art or may be prepared by procedures well known in the art.

When $R_3$ is methoxy or ethoxy in compound 1, an appropriate amino acid ester derivative is reacted with benzoyl halide, for example, chloride or an alkanoic acid halide, for example, chloride wherein the alkanoic acid has from 1 to 9 carbon atoms and may be straight or branched, such as, acetyl chloride, propionyl chloride, butyryl chloride, tert-butyryl chloride, 2,2-diethylbutyric acid chloride or valeryl chloride, at 0° C. in ethers, methylenechloride, dimethylformamide, dimethylacetamide or chlorobenzene in the presence of an organic base such as triethylamine or pyridine after which the reaction mixture is allowed to warm to about 25° C. for one hour. The resulting amide derivative is combined with an alkylating reagent, such as, methylfluorosulfonate, dimethylsulfate, methyliodide, methyl p-toluenesulfonate or trimethyloxonium hexafluorophosphate when $R_3$ is methoxy or triethyloxonium tetrafluoroborate when $R_3$ is ethoxy at about 25° C. in a chlorinated hydrocarbon solvent such as methylene chloride, chlorobenzene or chloroform, and the reaction mixture is refluxed for about 12 to 20 hours. The mixture is then cooled to about 25° C. and an organic base such as triethylamine or pyridine is added after which the solution is extracted with brine and the product isolated.

When $R_3$ and $R_4$ together form an alkylene group in compounds 1 of from 5 to 7 carbon atoms said amino acid ester derivatives are obtained by treating the amino acid ester with a cyclic alkanone selected from cyclopentanone, cyclohexanone and cycloheptanone to form a Schiff's base by procedures generally known in the art.

When in compounds 1, the symbol $Z_1$ is

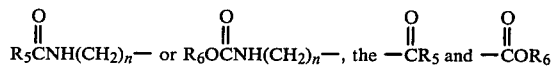

protecting groups are added to the corresponding free amino acids, that is, ornithine and lysine, by treatment of said amino acid with an excess of copper salt, for example, copper carbonate in boiling water for about 1 to 6 hours, and upon cooling to room temperature the insoluble materials are filtered off, and the filtrate is treated with an appropriate acid halide when $Z_1$ is

or an appropriate alkyl or aryl haloformate when $Z_1$ is

for example, in acetone in the presence of a base such as sodium bicarbonate or sodium hydroxide followed by treatment with hydrogen sulfide. Illustrative acid halides which may be employed are acetyl chloride, propionyl chloride, benzoyl chloride or 2-phenylacetyl chloride. Illustrative haloformates which may be employed are benzyl chloroformate, phenyl chloroformate, methyl chloroformate or ethyl chloroformate.

The lactams of the compounds of general Formula I wherein $R_1$ is carboxy are prepared from the corresponding amino acid ester of the structure

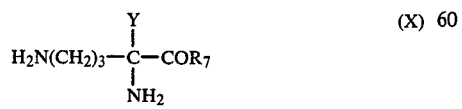

wherein Y has the meaning defined in Formula I and $R_7$ is a straight or branched alkoxy group of from 1 to 8 carbon atoms, illustratively methoxy, ethoxy, isopropoxy, butoxy or hexyloxy, by treating said amino acid esters with an appropriate base, such as, sodium hydroxide, potassium hydroxide, lithium hydroxide, sodium carbonate, potassium carbonate, sodium methoxide, potassium methoxide, potassium tert-butoxide, sodium amide, or an organic amine such as a trialkylamine, for example, triethylamine in a solvent such as a lower alcohol, for example, methanol, ethanol, isopropyl alcohol, n-butanol, water, dimethylformamide, dimethylsulfoxide, hexamethylphosphortriamide or mixtures of these solvents for from ½ hour to 24 hours at a temperature of from about 0° to 120° C. optionally under a nitrogen atmosphere. The compounds of general Formula X are obtained by procedures generally known in the art from the corresponding amino acid, for example, by treating said amino acid with an appropriate alcohol, for example, methanol, ethanol, isopropyl alcohol, n-butanol or n-heptanol saturated with HCl gas.

The compounds of general Formula I wherein Z is

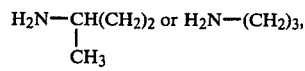

Y is $C\equiv CH$ and $R_1$ is carboxy are prepared by treating a suitably protected propargylamine derivative, such as a silyl derivative, with a strong base to form a protected propargylamine carbanion intermediate which is reacted with an alkylating reagent of the formula $R_8X$ wherein X is halogen, for example, chlorine or bromine, and $R_8$ is $PhHC=N(CH_2)_n$—wherein n is the integer 3 or 4; treating the thus formed alkylated protected propargylamine derivative with a strong base to form an alkylated protected propargylamine carbanion; reacting said second carbanion with an acylating reagent, and subsequently removing the protecting groups by acid or base hydrolysis as represented by the following reaction scheme:

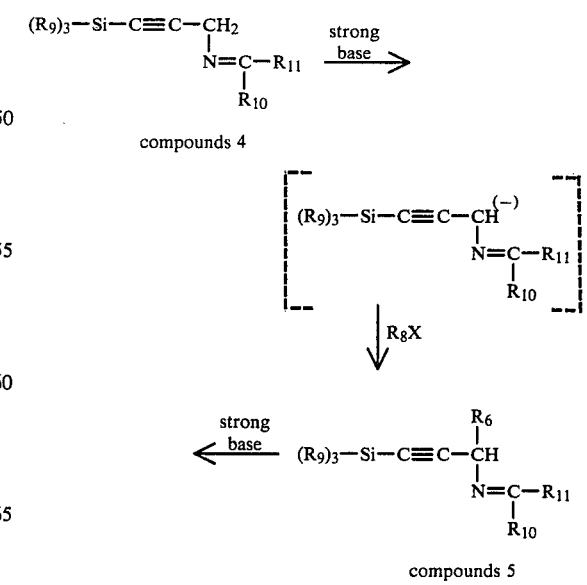

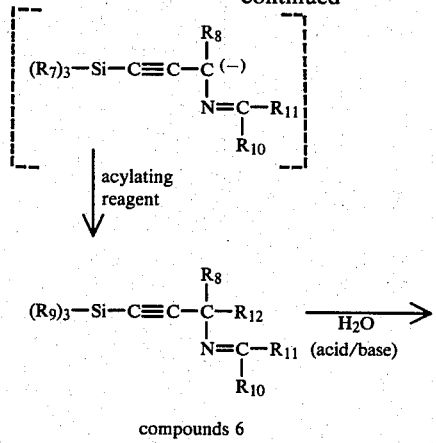

compounds 6

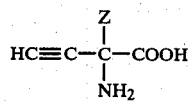

Formula XI in the above reaction scheme $R_8$ and X have the meanings defined hereinabove; Ph represents phenyl; $R_{10}$ is hydrogen, methoxy or ethoxy; $R_{11}$ is phenyl, tert-butyl, or triethylmethyl; $R_9$ is a straight or branched lower alkyl group having from 1 to 4 carbon atoms, such as, methyl, ethyl, n-propyl and tert-butyl; $R_{12}$ is a carboxy anion, a carboxylic acid ester, a carboxamide, a nitrile or other group capable of being hydrolyzed to a carboxylic acid function which varies with the acylating reagent employed; and Z is

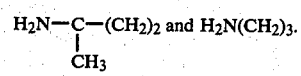

Suitable strong bases which may be employed in the above reaction to form each carbanion are those which will abstract a proton from the carbon atom adjacent to the acetylene moiety, such as, alkyl lithium, for example, butyl lithium or phenyl lithium, lithium di-alkylamide, for example, lithium diisopropylamide, lithium amide, tertiary potassium butylate or sodium amide.

The alkylating reagents, $R_8X$, employed in the above reaction are known in the art or can be prepared by methods known in the art. The reactant $PhHC=N(CH_2)_n$—can be prepared, for example, by reacting 3-bromo-n-propylamine hydrochloride or 4-bromo-n-butylamine hydrochloride with benzaldehyde in an organic amine, such as, triethylamine in a solvent such as diethyl ether, tetrahydrofuran, dioxane, chloroform or dichloromethane.

Suitable acylating reagents which may be employed in the above reaction are halo-formates, such as chloro methylformate or chloro ethylformate, azido tert-butylformate, cyanogen bromide, carbon dioxide, diethylcarbonate, phenylisocyanate, triethoxymethylium tetrafluoroborate, N,N-dimethylcarbamoyl chloride, 2-methylthio-1,3-dithiolinium iodide, ethylene carbonate or ethylene trithiocarbonate. When 2-methylthio-1,3-dithiolinium iodide is employed the additional step of alcoholysis with a lower alcohol, for example ethanol or isopropyl alcohol is required prior to deprotection by hydrolysis.

The alkylating reaction is readily conducted in the presence of an aprotic solvent, as for example, benzene, toluene, ethers, tetrahydrofuran, dimethylsulfoxide, dimethylformamide, dimethyl acetamide, hexamethyl phosphortriamide. For each reaction the temperature varies from $-120°$ C. to about $25°$ C., a preferred reaction temperature being about $-70°$ C., and the reaction time varies from about ½ hour to 24 hours.

Removal of the protecting groups, as represented in the reaction scheme in the step going from compounds 6 to compounds of Formula XI, is achieved by treatment with aqueous acid, for example, hydrochloric acid or toluene sulfonic acid, or aqueous base, for example, sodium hydroxide or potassium hydroxide. Optionally hydrazine or phenylhydrazine may be employed in removing the protecting groups.

The propargylamine derivatives, that is, compounds 4, wherein $R_{10}$ is hydrogen are prepared by the addition of protecting groups on the acetylene function and the nitrogen function of propargylamine. Protection of the nitrogen function of the propargylamine is accomplished by forming in a known manner a Schiff's base with a nonenolizable carbonyl bearing compound selected from benzaldehyde, 2,2-dimethylpropanal and 2,2-diethylbutanal. Protection of the acetylenic function is accomplished by reacting the above-described Schiff's base with a trialkylsilyl chloride wherein the alkyl moiety has from 1 to 4 carbon atoms and is straight or branched, for example, trimethylsilylchloride or triethylsilylchloride forming in a known manner the corresponding trialkylsilyl derivative.

The propargylamine derivatives, compounds 4, wherein $R_{10}$ is methoxy or ethoxy are prepared by reacting propargylamine wherein the acetylene function is protected by a trialkylsilyl group, wherein the alkyl moiety has from 1 to 4 carbon atoms and is straight or branched, with benzoyl chloride, pivalic acid chloride, or 2,2-diethylbutyric acid chloride at $0°$ C. in diethyl ether, dioxane, tetrahydrofuran, chloroform, methylenechloride, dimethylformamide, dimethylacetamide, or chlorobenzene in the presence of an organic base such as triethylamine or pyridine after which the reaction mixture is allowed to warm to about $25°$ C. for one hour. The resulting amide derivative is combined with an alkylating reagent, such as, methylfluorosulfonate, dimethylsulfate, methyliodide, methyl p-toluenesulfonate or trimethyloxonium hexafluorophosphate when $R_{10}$ is methoxy or triethyloxonium tetrafluoroborate when $R_{10}$ is ethoxy at about $25°$ C. in a chlorinated hydrocarbon solvent such as methylene chloride, chlorobenzene or chloroform, and the reaction mixture is refluxed for about 12 to 20 hours. The mixture is then cooled to about $25°$ C. and an organic base such as triethylamine or pyridine is added, after which the solution is extracted with brine and the product isolated.

The protected propargylamine starting material is obtained by treating a 3-trialkylsilylprop-2-ynyl-1-iminobenzyl derivative, that is compounds 4 wherein $R_{10}$ is hydrogen and $R_{11}$ is phenyl with hydrazine or phenylhydrazine at about $25°$ C. for about ½ hour after which the mixture is diluted with, for example, petroleum ether, benzene or toluene and the amine isolated. Alternatively the imine is hydrolyzed with 0.5 to 1 N HCl solution, and the aqueous phase evaporated to afford the amine hydrochloride.

Compounds of formula I wherein Z is

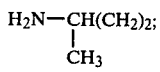

Y is $CH_2F$ or $CHF_2$; and $R_1$ is hydrogen are prepared by reducing a ketone of the formula

 (XII)

wherein Z' is

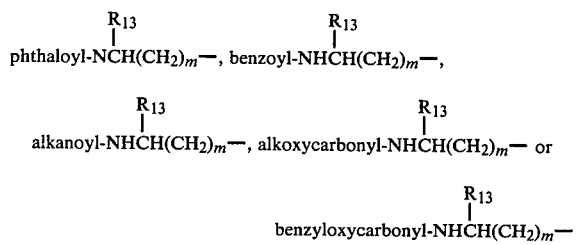

wherein m is an integer 2 or 3, the alkanoyl moiety has from 2 to 5 carbon atoms and is straight or branched, the alkoxy moiety has from 1 to 4 carbon atoms and is straight or branched, Y is $CH_2F$ or $CHF_2$ and $R_{13}$ is hydrogen or methyl. The ketones are reduced to the corresponding alcohol which is treated with one equivalent of an imide, such as, phthalimide, succinimide or maleimide, 1.1 equivalents of a phosphine, for example, triphenylphosphine or a trialkylphosphine, such as, tri-n-butylphosphine and 1.1 equivalents of diethyl azodicarboxylate in a suitable solvent, such as ethers, for example, diethyl ether, tetrahydrofuran or p-dioxane, benzene or dimethoxyethane at about 0° to 100° C., preferably about 25° C. for about one-half hour to 24 hours under an inert atmosphere, for example, nitrogen or argon and hydrolyzing the thus obtained imido derivative to the free amine.

The compounds of general formula (XII) wherein Y is $FCH_2$- are prepared by treating a compound of the formula

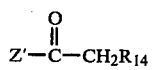 (XIII)

wherein Z' is defined as above and $R_{14}$ is a suitable leaving group, such as, halogen, for example, chlorine, bromine or iodine, mesylate, tosylate, triflate or trifluoroacetate with an appropriate fluorinating reagent, such as, potassium fluoride, silver fluoride, cesium fluoride, thallium fluoride, tetrabutylammonium fluoride in a suitable solvent, such as dimethoxyethane, dimethylsulfoxide, dimethylformamide, ethylene glycol, acetonitrile, acetone, benzene or hydrogen fluoride at a temperature of from about 0° to 200° C. for about 2 to 48 hours. The leaving group $R_{14}$ may also be a diazo group in which case the fluorinating reagent employed is hydrogen fluoride/pyridine. Suitable solvents for the reaction wherein $R_{14}$ is a diazo group are aprotic solvents, such as, diethyl ether, tetrahydrofuran and pentane, and the reaction time varies from about 30 minutes to 24 hours at a temperature of about −20° to 65° C. Illustratively, a compound of the formula

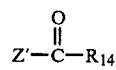

as defined above wherein $R_{14}$ is a diazo group in a suitable aprotic solvent is added to a solution of hydrogen fluoride/pyridine cooled to −10° C. The reaction mixture is stirred vigorously at −10° C. for 1 hour then at about 25° C. for 2 hours then poured on ice. The organic phase is separated, washed with base, for example, sodium bicarbonate, dried over magnesium sulfate and concentrated under vacuum to afford an appropriate fluoromethyl ketone derivative of formula (XII).

The diazo ketone derivatives, that is, the compounds of formula (XIII) wherein $R_{14}$ is a diazo group, may be obtained from the corresponding acid halide, that is, a compound of the formula

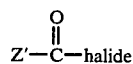

wherein halide may be, for example, chloride and Z' has the meaning defined in formula (XII) by slowly adding said acid halide in an aprotic solvent, such as, diethyl ether, tetrahydrofuran, pentane, hexane, benzene, dimethoxyethane or dioxane to a solution of diazomethane cooled to about −40° to 20° C. in ether followed by vigorous stirring at about 25° C. for about 1 to 24 hours. The thus obtained diazo ketone derivative can be isolated by standard procedures, for example, evaporation of the solvent with purification by recrystallization or chromatography or can be treated without isolation with an appropriate fluorinating reagent as described above.

The appropriately substituted diazo ketone derivative described above can also be used to prepare compounds of formula (XIII) wherein $R_{14}$ is, for example, halogen, mesylate, tosylate, triflate, or trifluoroacetate by procedures generally known in the art. To obtain compounds of general formula (XIII) wherein $R_{14}$ is halogen, such as, chlorine, bromine, or iodine the corresponding compound of formula (XIII) wherein $R_{14}$ is a diazo group in a suitable aprotic solvent is treated respectively with aqueous hydrogen chloride, hydrogen bromide or hydrogen iodide. To obtain compounds of formula (XIII) wherein $R_{14}$ is mesylate, tosylate, triflate or trifluoroacetate the corresponding diazo ketone derivative, that is, an appropriate compound of formula (XIII) wherein $R_{14}$ is a diazo group in a suitable aprotic solvent is treated with dilute sulfuric acid to give the corresponding benzyl methanol ketone derivative which is esterified with an appropriate acid chloride or acid anhydride of methane sulfonic acid, p-toluene sulfonic acid, trifluoromethyl sulfonic acid or trifluoroacetic acid.

The acid halides, that is, compounds of the formula

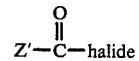

as described above, are known in the art or obtained from the corresponding acids which are known in the art or can be obtained by procedures known in the art by well known procedures, for example, by treatment of the appropriate acid with thionyl chloride in an aprotic solvent, such as, diethyl ether, tetrahydrofuran, benzene or dichloromethane at a temperature ranging from about 0° C. to the reflux temperature of the solvent for about 1 to 24 hours, or treatment of the appropriate acid with oxalyl chloride in an aprotic solvent as illustrated above at a temperature of about 0° to 40° C. for about 1 to 24 hours.

The compounds of general formula (XII) wherein Y is FCH$_2$— and Z' is other than benzoyl

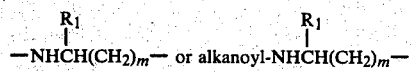

may also be obtained by treating a compound of the formula $$Z_2-R_{15} \qquad \qquad XIV$$

wherein Z$_2$ is

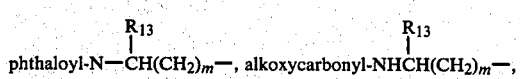

benzyloxycarbonyl -NHCH(CH$_2$)$_m$—, wherein m is the integer 2 or 3 and R$_{13}$ is hydrogen or lower alkyl of from 1 to 4 carbon atoms with the proviso that when R$_{13}$ is other than hydrogen m is 2, 3-methylthioethyl or 3-benzylthioethyl and R$_{15}$ is halogen, such as, chlorine, bromine or iodine, mesylate or tosylate with triphenylphosphine or tri-(lower)-alkylphosphine, for example, tri-n-butylphosphine, in a solvent such as hydrocarbons, for example, benzene or toluene or lower alcohols, such as, methanol or ethanol or acetonitrile, tetrahydrofuran, diethyl ether or dimethoxyethane at about 25° C. to the reflux temperature of the solvent for about 10 minutes to 48 hours. On cooling a precipitate forms which is washed with solvent and recrystallized using, for example, ethyl acetate, acetonitrile, or a lower alcohol, for example, methanol or ethanol to give the appropriate phosphonium salt. The triphenylphosphonium or trialkylphosphonium salt is added to excess (up to 25%) sodium or lithium metal dissolved in liquid ammonia to which is added a catalytic amount of ferric nitrate with stirring for about 10 minutes to 3 hours after which the ammonia is evaporated under an inert atmosphere, such as, nitrogen or argon. An appropriate solvent, such as, benzene, toluene, diethyl ether, tetrahydrofuran or dimethoxyethane is added and the resulting substituted methylidenephosphorane is collected. The methylidenephosphorane is treated with an ester, such as, a lower alkyl, for example, methyl, ethyl, n-propyl, isopropyl or n-butyl ester of monofluoroacetic acid in a solvent such as benzene, toluene, diethyl ether, tetrahydrofuran or dimethoxyethane under an inert atmosphere such as nitrogen or argon at a temperature of about 0° C. to the reflux temperature of the solvent for about 30 minutes to 24 hours after which the reaction mixture is concentrated and distilled to give the olefin which is treated with aqueous mineral acid, such as hydrochloric or hydrobromic acid or an organic acid such as trifluoroacetic acid or p-toluene sulfonic acid using a cosolvent such as tetrahydrofuran, diethyl ether, or benzene for about 30 minutes to 24 hours at a temperature of from about 0° C. to the reflux temperature of the solvent. The amount of acid employed may vary from a catalytic amount to concentrated acid.

As used in general formula (XIV) the term

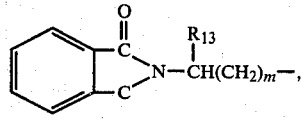

is taken to mean the group

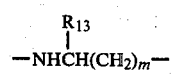

the term alkoxycarbonyl

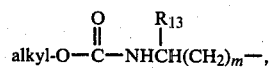

is taken to mean the group

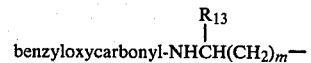

the term

benzyloxycarbonyl-NHCH(CH$_2$)$_m$— is taken to mean the group

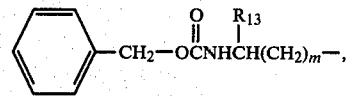

wherein R$_{13}$ and m have the meanings defined in formula (XIV) and alkyl is a straight or branched group of from 1 to 4 carbon atoms.

Compounds of general formula (XII) wherein Y is F$_2$CH- are obtained by treating [[(methylsulfinyl)methyl]-thio]methane or [[(ethylsulfinyl)methyl]thio]ethane with a suitable strong base followed by alkylation with an appropriate derivative of the formula $$Z'-R_{16} \qquad \qquad XV$$

wherein Z' has the meaning defined in formula (XII) and R$_{16}$ is halogen, such as, chlorine, bromine or iodine, mesylate or tosylate, treating the thus formed Z' substituted sulfinyl derivative with a suitable strong base followed by alkylation with a suitable halomethylhalo alkylating reagent selected from chlorodifluoromethane, bromidifluoromethane, and difluoriodomethane followed by hydrolysis with aqueous acid.

Suitable strong bases which may be employed in preparing the difluoromethyl substituted ketone derivatives as described above are illustratively, sodium hydride, dilithium acetylide, lithium diisopropylamide, butyllithium, potassium tert-butoxide, sodium tert-butoxide, lithium tert-butoxide, phenyllithium, methyllithium, sodium amide, lithium amide or potassium hydride.

The alkylation reactions described in preparing the difluoromethyl ketone derivatives are carried out in a suitable solvent, such as, tetrahydrofuran, diethyl ether, hexamethylphosphortriamide, dimethylsulfoxide, or benzene at a temperature ranging from about −78° to 65° C. for about 30 minutes to 24 hours. A preferred temperature for the difluoromethyl alkylation step is about 40° C. The alkylated sulfinyl intermediates are isolated by quenching with brine followed by extraction with, for example, diethyl ether, dichloromethane, or benzene.

Hydrolysis of the alkylated sulfinyl derivatives to the ketone is achieved using aqueous mineral acid, such as, hydrochloric, hydrobromic, perchloric or sulfuric in a solvent such as tetrahydrofuran, acetonitrile, diethyl ether or benzene at about −20° to 105° C., preferably about 25° C. for about 30 minutes to 24 hours and preferably about 2 hours. Generally, 0.3 equivalents of mineral acid in 1.5% water is employed. The specific examples contained herein further illustrate the preparation of the difluoromethyl ketone derivatives of formula (XII).

The compounds of formulas (XIV) and (XV) wherein $R_{15}$ and $R_{16}$ are halogen are known in the art or may be prepared from the appropriate carboxylic acid derivative of the formula $$Z_4\text{—COOH} \quad\quad\quad XVI$$

wherein $Z_4$ is

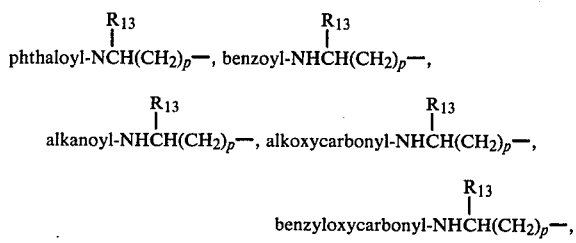

phthaloyl-NCH(CH$_2$)$_p$—, benzoyl-NHCH(CH$_2$)$_p$—, alkanoyl-NHCH(CH$_2$)$_p$—, alkoxycarbonyl-NHCH(CH$_2$)$_p$—, benzyloxycarbonyl-NHCH(CH$_2$)$_p$—, methylthiomethyl or benzylthiomethyl wherein p is the integer 1 or 2, which acids are known in the art or may be obtained by known procedures from the corresponding unprotected amino acids which are known in the art or readily obtained by procedures known in the art. The compounds of formulas (XIV) and (XV) wherein $R_{15}$ and $R_{16}$ are mesylate or tosylate may be prepared by treating the corresponding derivatives wherein $R_{15}$ and $R_{16}$ are halogen with a metal salt for example, the sodium salt of methane sulfonic acid or p-toluene sulfonic acid.

Reduction of the ketones of formula (XII) to the corresponding alcohol is achieved chemically using, for example, 1 to 10 equivalents of a metal hydride reducing reagent, such as lithium borohydride, sodium borohydride, sodium cyanoborohydride, or lithium aluminum hydride, borane or dimethylthioborane or catalytically using, for example, Raney nickel, rhodium, palladium on charcoal, or platinum oxide. Overall the reaction time varies from about 10 minutes to 24 hours and the temperature varies from about −40° C. to 100° C. depending on the reducing reagent employed. When chemical reduction is employed the reaction time generally varies from about 10 minutes to 24 hours with temperatures varying from about −40° C. to 65° C. Suitable solvents for chemical reduction of compounds of general formula (XII) include lower alcohols, such as, methanol or ethanol or ethers, such as, diethyl ether or tetrahydrofuran. When catalytic reduction is employed the reaction time varies from about 1 hour to 24 hours, the reaction temperature varies from about 25° to 100° C. and the pressure varies from 1 to 120 atmospheres.

Hydrolysis to the amine and to remove any distal amine protecting group is achieved using a strong mineral acid, for example, hydrochloric acid, hydrobromic acid or sulfuric acid or an organic acid, for example, toluene sulfonic acid or trifluoroacetic acid in water at reflux temperature for about 4 to 48 hours, or using, for example, 1 to 3 equivalents of hydrazine, methylhydrazine or methylamine at a temperature of from about 25° C. to reflux for about 1 to 12 hours followed by treatment with a strong mineral acid or organic acid as described above.

Compounds of formula I wherein Z is

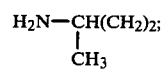

$$H_2N\text{—}\underset{\underset{CH_3}{|}}{CH}(CH_2)_2;$$

Y is C≡CH, or as hereinafter indicated the alkynyl group, and $R_1$ is hydrogen are prepared by hydrolysis of the alkylated compounds 5, described above. The desired alkylating reagents $R_8X$ that are employed can be prepared by methods known in the art. Thus, the reagent $$PhC\text{=}NCH_2(CH_2)_n\text{—}$$

can be prepared by reacting 3-bromo-n-propylamine hydrochloride or 4-bromo-n-butylamine hydrochloride with benzaldehyde and an organic amine, such as, a trialkylamine, for example, triethylamine in a solvent such as an ether, for example, diethyl ether, tetrahydrofuran or dioxane, chloroform or dichloromethane. The reactant $$PhHC\text{=}\underset{\underset{CH_3}{|}}{N}CH(CH_2)_n\text{—}$$

wherein n is the integer 2 is prepared by reacting 3-aminobutylbromide hydrobromide with benzaldehyde and an organic amine such as triethylamine. The γ-aminoalkanol derivative is obtained by treating an appropriate β-ketoalkanoic acid ester of the formula $$CH_3\overset{O}{\overset{\|}{C}}\text{—}CH_2\overset{O}{\overset{\|}{C}}\text{—}OCH_2CH_3$$

with hydroxylamine hydrochloride and reducing the resulting oxime by lithium aluminum hydride reduction.

The alkylating reaction may be carried out in an aprotic solvent, for example, benzene, toluene, ethers, tetrahydrofuran, dimethylsulfoxide, hexamethyl phosphortriamide. The reaction temperature varies from about −100° to 25° C. preferably about −70° C. and the reaction time varies from about ½ hour to 24 hours.

Removal of the protecting groups, as represented in the reaction scheme in the step going from compounds 5 to the desired amines, is achieved by treatment with aqueous acid, for example, hydrochloric acid followed by aqueous base, for example, sodium hydroxide or potassium or treatment with phenylhydrazine, hydroxylamine or hydrazine then with aqueous base.

The individual optical isomers of compounds of formula 1 wherein $R_1$ is carboxy or hydrogen are resolved using a (+) or (−) binaphthylphosphoric acid salt in accordance with the procedure of R. Viterbo et al., Tetrahedron Letters 48, 4617 (1971). Other resolving agents such as (+) camphor-10-sulfonic acid may also be employed. Alternatively, when Z is

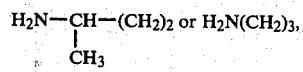

resolution is achieved via the lactam of said compounds. The thus resolved acids and amines may be employed in the same manner as described hereinabove for the racemic mixtures.

The compounds described herein are useful for their ability to inhibit the growth of algae. At present, copper sulfate is a commonly employed algicide. In alkaline water copper sulfate quickly precipitates as copper carbonate and more slowly as copper hydrate. Moreover, certain algae, as for example, the green alga Scenedesmus and the blue-green alga Chlorella are resistant to copper sulfate toxicity. Inasmuch as copper sulfate operates via a toxic response to algae, there still remain the difficult problems of odor, water palatability and the removal of dead and decomposing algae.

Thus, there is a need for economically feasible chemical compounds that are non-toxic to plants and animal life. It would further be highly desirable to have a biological agent which would effectively inhibit the growth and proliferation of algae in recreational and industrial water supplies, thereby eliminating, at the same time, the ancillary problems associated with dead and dying algae.

The α-substituted amines and α-substituted-α-amino acids of general formula (1) above are useful in controlling the growth of algae, e.g., in ponds, lakes, reservoirs, raw water supplies, water-treating plants, water-cooling towers, recreational waters, fish ponds and aquariums. Moreover, these compounds are effective in inhibiting algal growth of the major groups of algae, i.e., the blue-green algae, green algae, diatom algae and flagellate algae.

It is not exactly known how the compounds of this invention are able to inhibit the growth of algae. Inter alia, these compounds are irreversible inhibitors of ornithine decarboxylase and S-adenoxylmethionine decarboxylase. As irreversible inhibitors of these decarboxylase enzymes these compounds inhibit polyamine formation which may be required for algal cell division. In any event, the practice of this invention is not limited to any particular mode or theory of action whereby the compounds of this invention are able to effectively inhibit the growth of algae.

The effect of the compounds of general formula (1) above upon algal growth can be demonstrated by incubating the algae to be tested in a standard culture medium at room temperature and comparing the cell growth of the treated algae with the corresponding untreated control cultures. Cell growth and/or inhibition is determined in one of two ways, viz. by actual cell count of suitable samples, or by a comparison of the total cell weight, as illustrated in Example 13 below.

When dealing with large volumes of water such as lakes, reservoirs, or industrial water supplies, the α-substituted amines and α-substituted-α-amino acids of general formula (1) above can be utilized by casting the compounds directly upon the surface of such waters. Preferably, when utilized in this fashion, the compounds are formulated in a granular form. Alternatively, when dealing with smaller volumes of water, the compounds described herein can be dissolved in water to form a concentrate or stock solution, thereby permitting a more accurate control of the amount of compound to be administered.

The compounds described herein can be favorably employed at concentrations ranging from about 0.01 mg/ml to about 25 mg/ml. Preferably, a concentration of from 2 mg/ml to 15 mg/ml of active ingredient is employed.

The invention described herein is more particularly illustrated in conjunction with the following examples specifically describing how the compounds of this invention may be prepared and used.

EXAMPLE 1

2-Difluoromethyl-2,5-diaminopentanoic acid

Under nitrogen a solution (500 ml) of 2 M butyllithium in hexane is added to a stirred solution of 143.1 ml of diisopropylamine in 1.5 liters of tetrahydrofuran at −78° C. after which 261 g (0.81 mole) of ornithine dibenzaldimine methyl ester in 1.5 liters of tetrahydrofuran is added. Upon completion of the addition the reaction temperature is raised to 40° C. and maintained between 40° and 50° C. for 3 hours during which time chlorodifluoromethane gas is bubbled through the mixture with stirring. The reaction mixture is then treated with a saturated solution of sodium chloride. The organic material is extracted with ether, and the ether extract washed several times with sodium chloride solution, dried over magnesium sulfate and evaporated to give a viscous oil. The oil is stirred with 1 N HCl (1.5 l) for 3 hours, the mixture extracted several times with chloroform and the aqueous solution evaporated to dryness. The oily residue is refluxed with 12 N hydrochloric acid (1.5 l) for 16 hours, the cooled solution clarified by chloroform extraction before concentration, decolorization (charcoal), and further concentration to about 750 ml. The pH of the solution is adjusted to 3.5 by the addition of triethylamine, the solution treated again with charcoal before concentration to about 500 ml and dilution with 7–8 liters of acetone. The precipitated product is filtered off and washed with ethanol. The crude product is recrystallized by dissolving in about 150 ml hot water and treatment of the solution with hot ethanol (450 ml). On cooling crystals of 2-difluoromethyl-2,5-diaminopentanoic acid hydrochloride monohydrate separate 71 g (37%), m.p. 183° C.

EXAMPLE 2

α-Ethynyl-α,δ-diaminovaleric acid 11.8 g (0.048 M) of N-(3-trimethylsilylprop-2-ynyl)-benzenecarboximidate in 20 ml of tetrahydrofuran is added to lithium diisopropylamide, prepared from 4.9 g (6.78 ml, 0.048 M) of diisopropylamide in 60 ml of tetrahydrofuran and 23.6 ml of a 2.05 M solution of n-butyllithium at −70° C. after which 9.5 g (0.042 M) of N-(3-bromopropyl)benzylimine is added, and the mixture is stirred at −70° C. for 5½ hours. To the reaction mixture is added 23.6 ml of a 2.05 M solution of n-butyllithium followed by the addition of 4.5 g (3.67 ml, 0.048 M) of methyl chloroformate. After 30 minutes at −78° C. the mixture is treated with brine, and the reaction product is isolated by ether extraction. The ether extract is evaporated and 300 ml of 3 N HCl is added to the resulting residue and the mixture is refluxed for 7 hours. On cooling the mixture is washed well with methylene chloride, made alkaline and washed again. The aqueous solution is acidified and concentrated to dryness. The residue is triturated with ethanol, filtered and the ethanol evaporated. The residue is dissolved in water, the pH adjusted to 6, and the solution is applied to a column of Amberlite 120 H+, eluting with 1 M NH4OH which affords, upon recrystallization from ethanol-water, α-ethynyl-α,δ-diaminovaleric acid, M.P. 168–169 (dec.).

In the above procedure N-(3-bromopropyl)benzylimine is prepared from 3-bromopropylamine and benzaldehyde by procedures generally known in the art.

EXAMPLE 3

1-Fluoromethyl-4-methyl-1,4-butanediamine dihydrochloride

To a solution of 40 mmole of diazomethane in 110 ml of ether cooled to 0° C. and magnetically stirred is added under nitrogen dropwise over a period of 1 hour a solution of 20 ml of 4-phthalimido-4-methylbutyryl chloride in 75 ml of ether. Stirring is continued for 1 hour at 25° C. after which the reaction mixture is added to a solution of 40 ml of HF/pyridine precooled to 0° C. The resulting heterogeneous mixture is stirred at 25° C. for 1½ hours and then poured on ice water. The ether phase is separated, washed with a solution of bicarbonate, then with brine and dried over magnesium sulfate. Concentration of the solvent under reduced pressure affords a solid which is recrystallized from diethylether/pentane to give fluoromethyl 3-phthalimido-3-methylpropyl ketone.

To a solution of 550 mg (2.2 mmole) of fluoromethyl 3-phthalimido-3-methylpropyl ketone in a mixture of 5 ml of tetrahydrofuran and 5 ml of methanol cooled to −20° C. is added a solution of 0.8 mmole of sodium borohydride in a mixture of 5 ml of tetrahydrofuran and 5 ml of methanol precooled to −20° C. The reaction mixture is stirred for 15 minutes at −20° C. and then neutralized with 2 M HCl to a pH of 1. The solvents are evaporated under reduced pressure and the residue is partitioned between water and chloroform. The organic phase is washed and brine, dried over magnesium sulfate and concentrated to give a residue which is recrystallized from tetrahydrofuran-diethylether to afford 1-fluoro-5-phthalimido-5-methyl-2-pentanol. A mixture of 264 mg (1.05 mmole) of 1-fluoro-5-phthalimido-5-methylpentanol, 170 mg (1.05 mmole) of the phthalimide, 302 mg (1.05 mmole) of triphenylphosphine and 201 mg (1.15 mmole) of diethylazodicarboxylate in 8 ml of tetrahydrofuran is stirred under nitrogen for 2 hours at 25° C. The solvent is evaporated under reduced pressure and the residue taken up in benzene. The insoluble material is discarded and the residue obtained after concentration of the filtrate is recrystallized from tetrahydrofuran-diethylether to give 1-fluoromethyl-4-methyl-1,4-butanediyl-bis-phthalimide. A suspension of 3.1 g of 1-fluoromethyl-4-methyl-1,4-butanediyl-bis-phthalimide in 140 ml of concentrated HCl is heated at reflux temperature for 3 days. The phthalic acid which precipitates on cooling to 4° C. is filtered off. The filtrate is concentrated to about 20 ml and cooled to 4° C. The remaining phthalic acid which separates is filtered off and the filtrate is concentrated under reduced pressure. The residue is treated with 40 ml of boiling isopropyl alcohol 3 times and then recrystallized from absolute ethanol to give 1-fluoromethyl-4-methyl-1,4-butanediamine dihydrochloride.

EXAMPLE 4

1-Ethynyl-4-methyl-1,4-butanediamine

To 10.8 g (0.05 M) of 3-trimethylsilylprop-2-ynyl-1-iminobenzyl in 500 ml of tetrahydrofuran under nitrogen atmosphere at −78° C. is added n-butyllithium (0.05 M). After 10 minutes the dark red carbanion is treated with 11.3 g (0.05 M) of 3-iodo-3-methylpropyl-1-iminobenzyl in 20 ml of tetrahydrofuran. After 3 hours at −78° C., 50 ml of water is added and the tetrahydrofuran is evaporated leaving a residue which is heated at reflux under nitrogen atmosphere with 100 ml of 6 N hydrochloric acid for 48 hours. Upon cooling the aqueous solution is washed with methylene chloride, made alkaline with aqueous sodium hydroxide and reextracted with methylene chloride. The methylene chloride extract is dried over magnesium sulfate, filtered, concentrated and distilled to afford 1-ethynyl-4-methyl-1,4-butanediamine, b.p. 50° C./0.4 mm.

EXAMPLE 5

Granules suitable for distribution over large areas of water are prepared as follows.

|  | Grams |
| --- | --- |
| 2-Difluoromethyl-2,5-diaminopentanoic acid | 33.0 |
| Corn starch | 18.5 |
| Lactose | 48.2 |
| Zinc stearate | 0.3 |
|  | 100.0 |

The 2-difluoromethyl-2,5-diaminopentanoic acid and approximately 6 to 9 grams of the lactose are mixed and passed through a fluid energy mill or micronizer to give a particle powder size of approximately 1–25 microns. Water, 35 ml, is added to approximately 2.0 grams of the corn starch and blended to prepare a 5% starch paste. The micronized pentanoic acid-lactose powder, the remaining lactose and the remaining corn starch are well blended, the starch paste added and blended, and the resulting mixture passed through a No. 12 mesh screen. The resulting granules are dried at 38° C. to a moisture content of approximately 3%. The dried granules are ground through a U.S. Standard No. 12 screen and lubricated by mixing with 0.3 grams of zinc stearate.

EXAMPLE 6

A 20% stock solution of algae inhibitor for use in aquariums is prepared by dissolving 75.7 grams of 2-difluoromethyl-2,5-diaminopentanoic acid in one gallon of water. The addition of 90 ml of this stock solution to each gallon of water is sufficient to provide an effective algae inhibiting concentration of 4.8 mg.ml.

EXAMPLE 7

Cultures of green algae, *Scenedesmus basilensus,* and blue-green algae, *Phormidium inundatum,* are obtained from the Environmental Monitoring and Support Laboratory, U.S. Environmental Protection Agency, Cincinnati, Ohio. The *Scenedesmus basilensus* culture is diluted with three parts of a modified Chu. No. 10 culture media containing the following:

| Chemical | gms/liter |
| --- | --- |
| $Ca(NO_3)_2 \cdot 4H_2O$ | 0.232 |

| Chemical | gms/liter |
| --- | --- |
| K$_2$HPO$_4$ | 0.01 |
| MgSO$_4$ . 7H$_2$O | 0.025 |
| Na$_2$CO$_3$ | 0.02 |
| Na$_2$SiO$_3$ . 5H$_2$O | 0.044 |
| Ferric citrate | 0.0035 |
| Citric acid | 0.0035 |
| Tris(hydroxymethyl)aminomethane | 1.00 |

The *Phormidium inundatum* culture is diluted with three parts of the modified Chu. No. 10 culture media above, excluding the Tris(hydroxymethyl)aminomethane, and including the following trace elements:

| | |
| --- | --- |
| H$_3$BO$_3$ | 2.4 × 10$^{-3}$ |
| MnCl$_2$ . 4H$_2$O | 1.4 × 10$^{-3}$ |
| ZnCl$_2$ | 4.0 × 10$^{-4}$ |
| CoCl$_2$ . 6H$_2$O | 2.0 × 10$^{-5}$ |
| CuCl$_2$ . 2H$_2$O | 1.0 × 10$^{-7}$ |

A stock solution of 3.6 grams of 2-difluoromethyl-2,5-diaminopentanoic acid in 10 ml of distilled water is prepared. Aliquots, 100 ml., of each of the diluted algal suspensions are transferred to duplicate sets of 250 ml Erlenmeyer flasks which contain:
(a) Control-1.3 ml of sterile water
(b) Stock solution, 0.33 ml, and 1.0 ml of sterile water to make a final concentration of 1.2 mg/ml
(c) Stock solution, 1.31 ml, to make a final concentration of 4.8 mg/ml.

The cultures and test compound are mixed and exposed to a 175-200 foot-candle fluorescent source of light of constant intensity and observed over a period of 10 days. The *Scenedesmus basilensus* cells are counted using a standard hemacytometer. On the other hand, *Phormidium inundatum* being a branched algae, the cells can not be counted. The following results are observed as the average of two separate culture flasks each. (The abbreviation DFMO represents the compound 2-difluoromethyl-2,5-diaminopentanoic acid.)

| *Scenedesmus basilensus* | Number of Cells |
| --- | --- |
| Control-initial | 5.31 × 10$^7$ |
| Control-day 10 | 27.7 × 10$^7$ |
| 1.2 mg DFMO/ml-day 10 | 37.7 × 10$^7$ |
| 4.8 mg DFMO/ml-day 10 | 19.0 × 10$^7$ |

Additionally, the total weight of algal growth is measured by centrifuging the cultures at the end of the 10 day period, removing the supernatant and drying the algal residue overnight in a vacuum oven. The weights observed are expressed in grams.

| | *Scenedesmus basilensus* | *Phormidium inundatum* |
| --- | --- | --- |
| Control weight-initial | — | 0.0160 |
| Control weight-day 10 | 0.0324 | 0.0334 |
| 1.2 mg DFMO/ml-day 10 | 0.0254 | 0.0184 |
| 4.8 mg DFMO/ml-day 10 | 0.0164 | 0.0164 |

I claim:
1. A method of inhibiting the growth of algae which comprises contacting said algae with an algal inhibiting amount of an α-substituted amino acid having the formula

$$Z-\underset{\underset{NH_2}{|}}{\overset{\overset{Y}{|}}{C}}-R_1$$

wherein
R$_1$ is carboxy;
Y is selected from the group consisting of CH$_2$F, CHF$_2$, CF$_3$ and C≡CH;
Z is selected from the group consisting of $$H_2N-(CH_2)_3, \quad H_2N-\underset{\underset{CH_3}{|}}{CH}-(CH_2)_2 \text{ and } H_2N-CH_2CH=CH;$$

and
the salts and individual optical isomers thereof.
2. A method according to claim 1 wherein Y is CHF$_2$.
3. A method according to claim 1 wherein Z is $$H_2N-\underset{\underset{CH_3}{|}}{CH}-(CH_2)_2 \text{ or } H_2N-(CH_2)_3.$$

4. A method according to claim 1 wherein the α-substituted amino acid is 2-difluoromethyl-2,5-diaminopentanoic acid.
5. A method according to claim 1 wherein the α-substituted amino acid or the α-substituted amine is in solution at a concentration of from 0.01 mg/ml to 25 mg/ml.

* * * * *